United States Patent
Buss et al.

(10) Patent No.: US 9,206,121 B2
(45) Date of Patent: Dec. 8, 2015

(54) METHOD FOR THE PRODUCTION OF D,L-METHIONINE

(71) Applicants: Dieter Buss, Wesseling (DE); Martin Steurenthaler, Singapore (SG); Michael R. Rinner, Singapore (SG); Stephan Kretz, Biebergemuend (DE); Hans Joachim Hasselbach, Gelnausen (DE); Caspar-Heinrich Finkeldei, Alzenau (DE); Martin Koerfer, Kahl (DE); Pablo Zacchi, Huerth (DE)

(72) Inventors: Dieter Buss, Wesseling (DE); Martin Steurenthaler, Singapore (SG); Michael R. Rinner, Singapore (SG); Stephan Kretz, Biebergemuend (DE); Hans Joachim Hasselbach, Gelnausen (DE); Caspar-Heinrich Finkeldei, Alzenau (DE); Martin Koerfer, Kahl (DE); Pablo Zacchi, Huerth (DE)

(73) Assignee: EVONIK DEGUSSA GmbH, Essen (DE)

( * ) Notice: Subject to any disclaimer, the term of this patent is extended or adjusted under 35 U.S.C. 154(b) by 0 days.

(21) Appl. No.: 14/671,435

(22) Filed: Mar. 27, 2015

(65) Prior Publication Data
US 2015/0197489 A1  Jul. 16, 2015

Related U.S. Application Data

(62) Division of application No. 14/227,418, filed on Mar. 27, 2014, which is a division of application No. 13/402,041, filed on Feb. 22, 2012, now Pat. No. 8,729,288.

(60) Provisional application No. 61/445,781, filed on Feb. 23, 2011.

(51) Int. Cl.
C07C 319/20 (2006.01)
C07C 51/08 (2006.01)
C07C 253/00 (2006.01)

(52) U.S. Cl.
CPC .................... C07C 319/20 (2013.01)

(58) Field of Classification Search
CPC .... C07C 253/10; C07C 255/16; C07C 253/08
See application file for complete search history.

(56) References Cited

U.S. PATENT DOCUMENTS

| 2,745,745 | A | 5/1956 | Blake et al. |
| 4,912,257 | A | 3/1990 | Hernandez et al. |
| 4,960,932 | A | 10/1990 | Gillonnier et al. |
| 5,498,790 | A * | 3/1996 | Grendel et al. ............... 562/581 |
| 5,663,409 | A | 9/1997 | Blackburn et al. |
| 5,756,803 | A | 5/1998 | Casse et al. |
| 5,866,379 | A * | 2/1999 | Burlingame et al. ......... 435/129 |
| 5,990,349 | A | 11/1999 | Geiger et al. |
| 6,126,972 | A | 10/2000 | Körfer et al. |
| 6,140,536 | A | 10/2000 | Hasseberg et al. |
| 6,150,563 | A | 11/2000 | Hasselbach et al. |
| 6,287,627 | B1 | 9/2001 | Binder et al. |
| 6,797,827 | B2 | 9/2004 | Körfer et al. |
| 7,119,228 | B2 | 10/2006 | Buss et al. |
| 7,119,233 | B2 | 10/2006 | Dubner et al. |
| 7,179,938 | B2 | 2/2007 | Weckbecker et al. |
| 7,199,270 | B2 | 4/2007 | Möller et al. |
| 7,655,072 | B2 | 2/2010 | Hasselbach et al. |
| 7,833,508 | B2 | 11/2010 | Redlingshöfer et al. |
| 8,624,066 | B2 | 1/2014 | Finkeldei et al. |
| 2006/0030739 | A1 | 2/2006 | Dubner et al. |
| 2011/0306784 | A1* | 12/2011 | May et al. ..................... 560/215 |
| 2012/0215021 | A1 | 8/2012 | Buss et al. |
| 2012/0215022 | A1 | 8/2012 | Buss et al. |
| 2013/0231501 | A1 | 9/2013 | Hasselbach et al. |
| 2013/0245318 | A1 | 9/2013 | Steffan et al. |
| 2014/0051890 | A1 | 2/2014 | Finkeldei et al. |

FOREIGN PATENT DOCUMENTS

| EP | 0330527 | 8/1989 |
| WO | WO 96/40631 | 12/1996 |
| WO | WO 2006/015684 | 2/2006 |

OTHER PUBLICATIONS

International Search Report issued Jul. 2, 2012 in Application No. PCT/EP2012/052367 (With English Translation of Category of Cited Documents).

* cited by examiner

*Primary Examiner* — Joseph Kosack
*Assistant Examiner* — Amanda L Aguirre
(74) *Attorney, Agent, or Firm* — Oblon, McClelland, Maier & Neustadt, L.L.P.

(57) ABSTRACT

A method to produce D,L-Methionine from 2-hydroxy-4-(methylthio)butyronitrile by reaction with ammonia, optionally in the presence of carbon dioxide, is provided. The 2-hydroxy-4-(methylthio)butyronitrile is obtained by reaction of 3-methylmercaptopropionaldehyde with hydrogen cyanide in the presence of a base as catalyst in a main reaction zone of a multizone reactor. Residual gaseous hydrogen cyanide is removed from the main reaction zone to an absorption and post-reaction zone of the reactor which comprises a mixture of 3-methylmercaptopropionaldehyde and the catalyst; and the gaseous hydrogen cyanide is further reacted with the 3-methylmercaptopropionaldehyde in the absorption and post reaction zone. A molar ratio of hydrogen cyanide to 3-(methylthio)propanal in the main reaction zone is from 0.98 to 1.03.

11 Claims, 1 Drawing Sheet

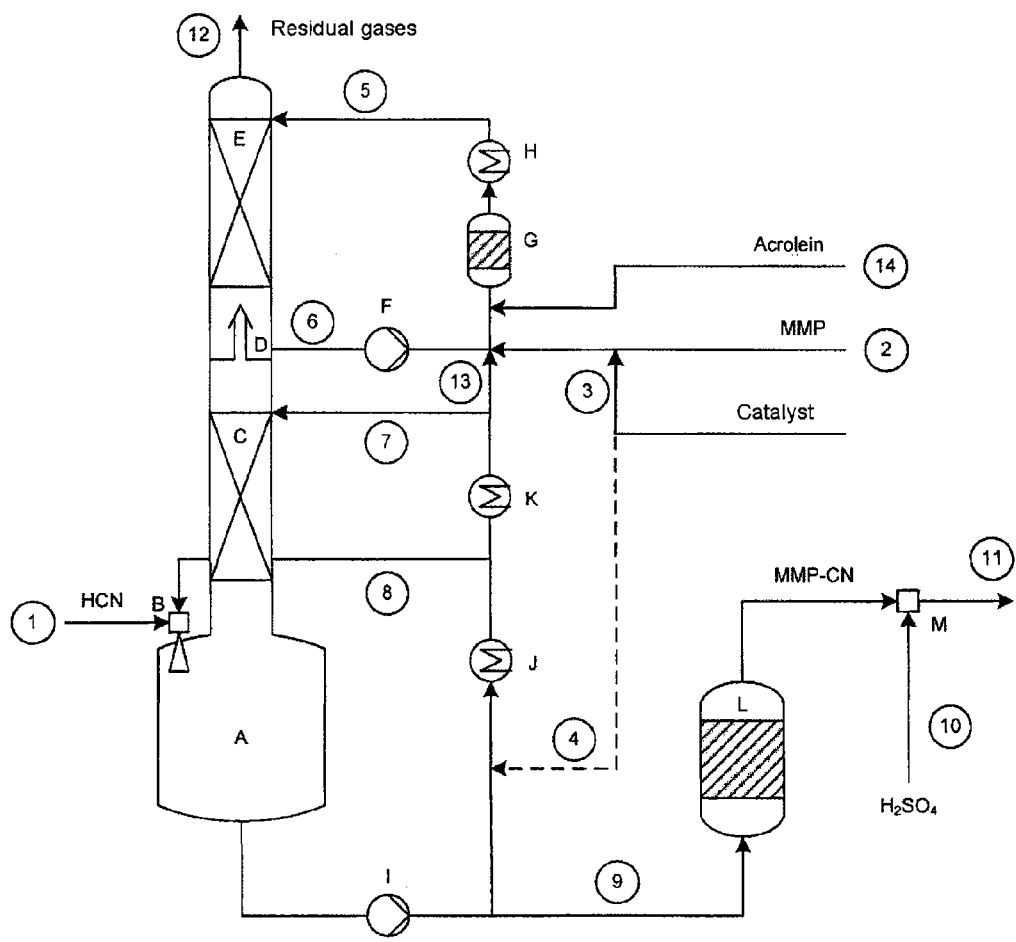

METHOD FOR THE PRODUCTION OF D,L-METHIONINE

CROSS REFERENCE TO RELATED APPLICATIONS

This application is a divisional application of prior U.S. application Ser. No. 14/227,418, filed Mar. 27, 2014, the disclosure of which is incorporated herein by reference in its entirety. The parent application is a divisional application of prior U.S. application Ser. No. 13/402,041, filed Feb. 22, 2012, the disclosure of which is incorporated herein by reference in its entirety. The grandparent application claims priority to U.S. Provisional Application No. 61/445,781, filed Feb. 23, 2011, the disclosure of which is incorporated herein by reference in its entirety.

BACKGROUND OF THE INVENTION

The invention relates to a catalytic method for the production of 2-hydroxy-4-(methylthio)butyronitrile (MMP-CN) from 3-(methylthio)propanal (=methylmercaptopropionaldehyde, MMP) and hydrogen cyanide (HCN). In particular, the invention describes a process for synthesizing storage-stable MMP-CN using stoichiometric amounts of prussic acid (HCN), the product containing superstoichiometric amounts of prussic acid, in relation to the unreacted MMP or to the MMP in equilibrium with MMP-CN.

2-Hydroxy-4-(methylthio)butyronitrile (MMP-cyanohydrin) is an intermediate for the synthesis of D,L-methionine and the methionine hydroxyl analog 2-hydroxy-4-methylthiobutyric acid (MHA). Methionine is an essential amino acid which is used, inter alia, as supplement in feedstuffs. MHA is a liquid methionine substitute having low bioavailability.

From MMP, by reaction with hydrogen cyanide (prussic acid), MMP-cyanohydrin (2-hydroxy-4-(methylthio)butyronitrile) may be produced using suitable catalysts. Suitable catalysts are, e.g., pyridine or triethylamine. By hydrolysis of MMP-cyanohydrin with, e.g., mineral acids, MHA is obtained. Methionine is formed by reaction of MMP-cyanohydrin with ammonium hydrogencarbonate, with formation of hydantoin, which can be saponified with a base, e.g. potassium carbonate or sodium hydroxide. Methionine is liberated with carbon dioxide or sulfuric acid.

It is known, for example, from the U.S. Pat. No. 4,960,932, to produce methionine by a four-stage method. In the first step, by addition of HCN to MMP in the presence of triethylamine, the MMP-cyanohydrin is produced. The amount of HCN used corresponds to 1.05 mol in relation to the amount of MMP used. Then, the MMP-cyanohydrin, in a second step, is reacted with ammonia, whereby 2-amino-4-methylthiobutyronitrile is formed which, in a third step, is then hydrolyzed in the presence of a ketone and an alkali metal hydroxide, forming methylthiobutyramide which is finally saponified to form an alkali metal methioninate.

In the case of production of 2-hydroxy-4-methylthiobutyric acid (MHA), the 2-hydroxy-4-methylthiobutyronitrile is obtained by reacting MMP and HCN in a medium that contains pyridine or an amine (see U.S. Pat. No. 2,745,745, column 2, lines 52 to 55). Excess HCN is merely distilled off, e.g. in a vacuum. The resultant 2-hydroxy-4-methylthiobutyronitrile is then hydrolyzed with sulfuric acid, whereby the amide of 2-hydroxy-4-methylthiobutyric acid is directly formed, and finally 2-hydroxy-4-methylthiobutyric acid is formed. A similar method is also described in EP A 330 527 A1 or in U.S. Pat. No. 4,912,257.

In addition, in WO 96/40631 A1, the production of MMP-cyanohydrin by reacting MMP with hydrogen cyanide in the presence of a suitable addition reaction catalyst is described. There it was found that triisopropanolamine, nicotinamide, imidazole, benzimidazole, 2-fluoropyridine, poly-4-vinylpyridine, 4-dimethylaminopyridine, picoline and pyrazine can serve as addition reaction catalysts for producing MMP-cyanohydrin. Furthermore, trialkylamines having three to eighteen carbon atoms in each of the alkyl substituents bound to the nitrogen atom and tertiary amines in which at least one of the non-hydrogen substituents that are bound to the nitrogen atom according to the above description contains an aryl group can also serve for catalyzing the reaction between MMP and hydrogen cyanide to form MMP-cyanohydrin.

Preferably, in this case, the hydrogen cyanide is used in a molar excess of about 2%, based on MMP.

WO 2006/015684 A2 finally discloses a method for, in particular, continuous production of MMP or of MMP-cyanohydrin in which in each case heterogeneous amine catalysts are used for the addition reaction.

In addition, it is known from the U.S. Pat. No. 5,756,803 to react an aldehyde with hydrogen cyanide in the presence of a buffer, by means of which the pH of the solution can be set above 4, amines being excluded. Quite generally, as buffer, mixtures of alkali metal salts of acids and acids, or mixtures of acids and alkali metal hydroxides can be used. The buffer is used in order firstly to avoid the decomposition of the starting materials and of the desired product and secondly to neutralize the acids used for stabilizing hydrogen cyanide. Likewise, here, HCN is added in a molar excess to the MMP, the molar excess preferably being in the range from 2% to 5%. In the reaction of MMP with HCN in the presence of the customarily used bases, although these increase the reaction rate under the conditions specified, they rapidly lead to a decomposition of the cyanohydrin formed and to decomposition of the aldehyde used at the start, forming a highly discolored solution.

In order to recover the residual amounts of unreacted HCN and MMP contained in the exhaust gas of the reactive absorber, said unreacted HCN and MMP are scrubbed using a water scrubber, the scrubbing water passing into the product. The water content in the product is approximately 48% by weight.

The substantial disadvantages of the methods previously described in the literature are that for achieving a high MMP-CN yield, high molar excesses of HCN have to be used. The excess amounts of HCN are lost in the methods described and are a great economic disadvantage. Furthermore, the catalysts used in the methods described also promote the formation of unwanted byproducts from the aldehydes used, which lead to contamination of the product which cannot be tolerated. One approach to solving this problem of formation of byproducts is described in U.S. Pat. No. 5,756,803 with, of course, large amounts of water passing into the product, which firstly, for production of methionine, need to be at least partially removed and which secondly again promote the decomposition of the MMP-cyanohydrin which in each case is a not inconsiderable disadvantage. Therefore, the product described in U.S. Pat. No. 5,756,803 is not storage stable and, for storage and in particular for transport, must be processed in a complex manner by means of removal of the water by distillation, which is a great economic disadvantage of the method.

SUMMARY OF THE INVENTION

One objective of this invention was to provide a catalytic method which both catalyzes the reaction of aldehyde, in particular of MMP with hydrogen cyanide, and prepares a storage-stable cyanohydrin in which the method provides greater yield and process efficiency with respect to the conventionally known methods.

This and other objectives are achieved according to the methods of the present invention, a first embodiment of which provides a method for producing 2-hydroxy-4-(methylthio) butyronitrile, comprising:

reacting 3-methylmercaptopropionaldehyde with hydrogen cyanide in the presence of a base as catalyst in a main reaction zone of a multizone reactor to form a reaction mixture comprising the 2-hydroxy-4-(methylthio)butyronitrile, unreacted 3-methylmercaptopropionaldehyde, the catalyst and residual amounts of gaseous hydrogen cyanide;

removing the residual gaseous hydrogen cyanide from the main reaction zone to an absorption and post-reaction zone of the reactor which comprises a mixture of 3-methylmercaptopropionaldehyde and the catalyst; and further reacting the gaseous hydrogen cyanide with the 3-methylmercaptopropionaldehyde in the absorption and post reaction zone.

In a highly preferred embodiment of the invention, a molar ratio of hydrogen cyanide to 3-(methylthio)propanal in the main reaction zone is from 0.98 to 1.03.

BRIEF DESCRIPTION OF THE DRAWINGS

The FIGURE shows a process flow diagram according to one embodiment of the invention.

DETAILED DESCRIPTION OF THE PREFERRED EMBODIMENTS

The first embodiment of the present invention provides a method for producing 2-hydroxy-4-(methylthio)butyronitrile, comprising:

reacting 3-methylmercaptopropionaldehyde with hydrogen cyanide in the presence of a base as catalyst in a main reaction zone of a multizone reactor to form a reaction mixture comprising the 2-hydroxy-4-(methylthio)butyronitrile, unreacted 3-methylmercaptopropionaldehyde, the catalyst and residual amounts of gaseous hydrogen cyanide;

removing the residual gaseous hydrogen cyanide from the main reaction zone to an absorption and post-reaction zone of the reactor which comprises a mixture of 3-methylmercaptopropionaldehyde and the catalyst; and further reacting the gaseous hydrogen cyanide with the 3-methylmercaptopropionaldehyde in the absorption and post reaction zone.

The residual content of HCN reacts, owing to the absorption or condensation with the aldehyde to form the cyanohydrin. Owing to the effective removal of the HCN from the gas phase, it is possible, in contrast to the methods known in the literature to use a molar ratio of hydrogen cyanide to aldehyde of 0.98 to 1.03, preferably 0.99 to 1.01, which is a great economic advantage for the method.

In one preferred embodiment, the invention provides a method for the addition reaction of hydrogen cyanide to MMP in the presence of a base, in particular an amine, wherein residual contents of gaseous hydrogen cyanide may be absorbed outside a main reaction zone into a liquid mixture at temperatures of about 0° C. to 25° C., the liquid mixture containing MMP, the reaction product from MMP with hydrogen cyanide and catalyst and then the absorbed HCN may be further reacted with the MMP. The described temperature range for the absorptive mixture includes all values therebetween, including 5° C. to 20° C. and 10° C. to 15° C.

In another preferred embodiment of the present invention, aldehydes containing 1 to 6 carbon atoms optionally substituted with alkyl, alkoxy or alkylthio, may be substituted for the MMP and reacted with hydrogen cyanide to obtain a corresponding cyanohydrin product.

In another preferred embodiment the mixture contained in the absorption and post-reaction zone may originate at least partially from the main reaction zone. A dilution with foreign materials or foreign solvents may thereby be avoided, in contrast, for example to the method disclosed in U.S. Pat. No. 5,756,803.

In separate embodiments, the main reaction zone may comprise either a stirred reactor or a loop reactor. Both embodiments may provide for rapid and efficient mixing of the reaction mixture and a rapid conversion of MMP and HCN to product.

In a highly preferred embodiment according to the invention, the main reaction zone may comprise a jet pump, for example as shown in the FIGURE. This equipment configuration may lead to a further intensification of mixing of the components and may be used concomitantly in a particularly advantageous embodiment to draw the gaseous HCN into the main reaction zone.

The reaction between the HCN-containing gas and liquid mixture in the post-reaction zone may be advantageously promoted by including a device for contacting a gas with a liquid in this zone. In particular, the device may be a column such as, for example, a tray column, a packed-bed column, a bubble-column reactor, a droplet column or optionally the device may be a reactor having a mechanically agitated container, or a submerged jet reactor.

In a highly efficient embodiment of the invention, the absorption zone and the post-reaction zone may be part of a loop reactor, which may effect high mixing and rapid reaction of the components.

According to one embodiment of the invention, the gaseous hydrogen cyanide introduced into the main reaction zone, may be a hydrogen-cyanide-containing product gas from a hydrogen cyanide production process which may be optionally directly connected to the reactor.

The hydrogen cyanide content of the gas mixture may be from 1 to 99% by weight, preferably from 5 to 75% by weight, particularly preferably 6-22% by weight. The hydrogen cyanide may be produced by the Andrussow method as per DE 102007034715A1 or else by the BMA method in German ("Blausäure aus Methan and Ammonik" [prussic acid from methane and ammonia]) as per DE 1041476 (reactor). Both methods are also described in Ullmann's Encyclopedia of Industrial Chemistry, 1987 VCH-Verlagsgesellschaft mbH, chapter "Cyano Compounds Inorganic", section 1.2.1-1.2.2. The ammonia present is removed in each case from the product gas. The product gas from the Andrussow method (Andrussow gas) contains, after the removal of ammonia, typically about 10% by weight of hydrogen cyanide, in contrast, the product gas from the BMA method (BMA gas) contains about 70% by weight of hydrogen cyanide.

Thus, the typical product gas composition obtained by the Andrussow method have approximately the following composition: 10.3% by weight of HCN, 3.7% by weight of $H_2O$, 1.3% by weight of $H_2$, 75.8% by weight of $N_2$, 0.4% by weight of $O_2$, 6.3% by weight of CO, 0.6% by weight of $CO_2$, 0.4% by weight of $CH_4$, 1.3% by weight of Ar, those of the BMA method about 68.3% by weight of HCN, 6.7% by weight of $H_2O$, 17.3% by weight of $H_2$, 3.6% by weight of $N_2$, 4% by weight of $CH_4$.

The direct use of such a product gas may have the considerable advantage that no upstream and energy-intensive liquefaction of the hydrogen cyanide need proceed and with corresponding coupling to a plant for producing hydrogen cyanide gas, considerable capital costs in corresponding process steps for the absorption and distillation of HCN may be saved. The further gas fractions in addition to HCN surprisingly do not have a disadvantageous effect on the cyanohydrin yield.

The residual gas of the MMP-cyanohydrin production and hydrogen cyanide production may then be utilized jointly or burnt. In the latter case, the resultant energy can be reused for operating both methods, which means more degrees of freedom and a considerable economic advantage.

One preferred embodiment of the method according to the invention and a corresponding device are shown in FIG. 1, which is described in more detail hereinafter:

When a tray column or a packed-bed column is used for the reactive absorption, the gas flow which contains the prussic acid is fed into the bottom phase (A) of the column (C) or preferably already contacted with the aldehyde solution via a gas blower (B), which aldehyde solution is circulated (8) by means of a pump (I). The temperature in the bottom phase of the column is set via a heat exchanger (J). The bottom phase (A) and the column (C), in particular, serve as the main reaction zone, the column C being able to be heated/cooled separately by means of a heat exchanger (K). In this case the temperature of the streams (7) and (8) is selected in such a manner that the heat of reaction can be removed with cooling water corresponding to the ambient temperature and the reaction between aldehyde and HCN in column part (C) is 80 to 99.9% complete.

The aldehyde may optionally be fed separately or together with the catalyst ((2), (3)). Preferably, the aldehyde or the aldehyde/catalyst mixture (2)+(3) is mixed with a substream (6) from the absorption and condensation part (E) of the column which is taken off from an intermediate bottom phase (D). The catalyst can also be fed, e.g., via the pathway (4). In this case, the catalyst should, via the pathway (13), also arrive in part in the top circuit. The residual amounts of HCN present in stream (6) are reacted with the supplied aldehyde in the dwell time vessel (G), the (second) post-reaction zone, completely or virtually completely to the cyanohydrin. Thereafter, the stream is cooled to 0° C. to 25° C. in the heat exchanger (H) in order to ensure condensation/absorption of HCN which is as complete as possible. In particular, the intermediate bottom phase (D), the absorption and condensation part (E) and the dwell time vessel (G) serve as absorption and post-reaction zone. Owing to the amounts of cyanohydrin present in the stream (5), and the cooling which is performed, the residual gases exiting at the column top also contain only very low residual amounts of the aldehyde, and so no additional scrubbing for recovery of the aldehyde from the residual gas is required. The cyanohydrin concentration can be set via corresponding metering from the column bottom phase (13), preferably in the range from 10% by weight to 70% by weight in stream (5). The purified gases are advantageously passed into a combustion unit. The product exiting with stream (9) has a molar ratio of hydrogen cyanide to unreacted aldehyde of greater than 1, which contributes substantially to stabilizing the product. In addition, the product is clear and only slightly discolored, which underlines the extraordinarily high selectivity of this process procedure.

After passage through a post reactor (L), in which any residual fractions of the aldehyde present are reacted to completion to achieve equilibrium with hydrogen cyanide, the resulting product stream is mixed with an acid. For this purpose, a suitable mixing element (M) may be used. The pH of the product (stream (11)) that is set in this case may be between 1 and 4, preferably between 2 and 3.

If the aldehyde is MMP, as shown in FIG. 1, the MMP starting material stream of the method described generally has a small content of methylmercaptan (MC), the predominant part of which would pass into the exhaust gas stream (12). This excess MC may also optionally be reacted with acrolein, which may be fed to the method, e.g. via stream (14), to form MMP and in succession with HCN to form MMP-CN and the yield thereby further increased.

In the method according to the invention, the catalyst may be low-molecular-weight or heterogeneous amines or solutions of inorganic bases, or mixtures of acids and low-molecular-weight amines. These may also be useful in order to set the optimum pH range of approximately 4.5 to 6.0, preferably 5.0-5.5, that may be required for the reaction, which is measured using a pH electrode ("Aquatrode Plus with Pt 1000" type, manufacturer: Metrohm Schweiz AG) directly in the cyanohydrin which typically contains 2-14% by weight of water. The measurements are performed at a temperature of about 23° in a stirred vessel, the pH measurement being temperature-compensated. For following the reaction conditions close in time, and for elimination of measurement errors, pH measurements may be completed at intervals of one hour, in each case the pH may be measured 4 times with determination of the mean value. Each measurement may take approximately 30 seconds. The measurement may, however, also be carried out directly during the reaction online in the reaction system at the temperature that is set there and converted to the pH at 23° C., which may further simplify the process control.

Low-molecular-weight amines, preferably having 1 to 36 carbon atoms, more preferably 6 to 30 carbon atoms, may have the particular advantage of virtually unlimited miscibility with the reaction medium, which in turn favors a rapid reaction.

Low-molecular-weight amines which may be preferred in this case are tri-($C_1$-$C_{12}$-alkyl)amines, preferably triethylamine or triisopropanolamine, dialkylaralkylamines, preferably dimethylbenzylamine, dialkylarylamines, preferably N,N-dimethylaniline, heterocyclic amines, preferably nicotinamide, imidazole, benzimidazole, 2-fluoropyridine, 4-dimethylaminopyridine, picoline or pyrazine.

Alternatively, heterogeneous amines of formula (I)

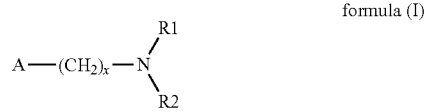

formula (I)

or polyvinylpyridine may also be used, wherein $R_1$ and $R_2$ are each, independently, hydrogen, alkyl having chain lengths between $C_1$ and $C_{12}$, aryl or heteroaryl;

X is a number between 0 and 6, and

A is a natural or synthetic resin, preferably a polystyrene. These and the advantages associated therewith, such as, for instance, easier separability, low entrainment in subsequent reaction stages, are described in WO 2006/015684.

It is preferred in this case that the catalyst according to formula (I) is a polymer-bound base selected from the group of the homologous dialkylaminoalkylpolystyrenes or dialkylaminomacroreticular resins.

It may be particularly preferred that the catalyst according to formula I is diethylaminoethylpolystyrene, diethylaminomethylpolystyrene, dimethylaminomethylpolystyrene, diethylaminomethylmacroreticular resin or dimethylaminoethylpolystyrene.

The inorganic base used may advantageously be alkali metal hydroxide, preferably NaOH or KOH, alkali metal cyanide, preferably NaCN or KCN, alkali metal carbonate, preferably $Na_2CO_3$ or $K_2CO_3$, or alkali metal hydrogencarbonate, preferably $NaHCO_3$ or $KHCO_3$, alone or in mixed form. These may have the advantage of particularly high catalytic activity which in turn favors a very rapid reaction and also the low potential interference of the low salt fractions resulting therefrom in the subsequent method. However, here, extremely good mixing and temperature control must be ensured, so that no significant byproduct formation proceeds.

As catalysts, advantageously, also mixtures of acids and the abovementioned low-molecular-weight amines may be used, in order to set the pH more readily in the desired range and to be able to stabilize it by the buffer action. Particularly advantageous in this case is the use of organic acids such as short-chain fatty acids, e.g. acetic acid, formic acid, citric acid, and organic sulfonic acids, e.g. trifluoromethanesulfonic acid or the use of mineral acids such as, e.g., sulfuric acid or phosphoric acid, in combination with the low-molecular-weight amines.

According to a further preferred embodiment of the invention, the temperature in the main reaction zone may be selected in such a manner that the heat of reaction liberated can be given off to cooling water in accordance with the ambient temperature, which may be a further great economic advantage of the method.

Correspondingly, the main reaction zone may be operated at a temperature of 20° C. to 80° C., preferably from 30° C. to 70° C., particularly preferably from 35° C. to 65° C. The reaction may also proceed comparatively rapidly in this range.

In the method according to the invention it may be further preferred that the absorption and post-reaction zone is operated at a temperature of 0° C. to 30° C., preferably from 4° C. to 15° C. This may ensure a particularly efficient absorption of the hydrogen cyanide and still makes possible thorough reaction of HCN with the MMP to form MMP-cyanohydrin.

Furthermore, the use of a second post-reaction zone just upstream of the product discharge point for the MMP-cyanohydrin is advantageous. This second post-reaction zone is operated at a similar temperature to the main reaction zone of 20° C. to 80° C., preferably 40° C. to 70° C., particularly preferably 45° C. to 65° C. In this manner a rapid and virtually quantitative completion of the reaction of HCN and MMP to form MMP-cyanohydrin shortly upstream of the product discharge may be ensured.

The method according to the invention may be advantageously operated at an absolute pressure of 0.9 to 5 bar, preferably 1.0 to 3 bar, particularly preferably 1 to 1.5 bar. This may have the effect that rapid degassing of the absorbed HCN from the solution and corresponding losses are thereby prevented.

The method according to the invention may employ, a molar ratio of prussic acid to 3-(methylthio)propanal of 0.98 to 1.03, preferably 0.99 to 1.01. Firstly, losses of prussic acid may thus be avoided which losses, especially on an industrial scale, would result in a great economic disadvantage. Secondly, unwanted prussic acid breakdown products such as, e.g., polymeric prussic acid or the saponification product formic acid which has corrosive properties against various metallic materials, may be avoided and corresponding disadvantageous effects in the downstream method stages to methionine may also thereby be avoided.

In the method according to the invention, preferably, a weight ratio of catalyst to 3-(methylthio)propanal of 0.00005 to 0.002 may be used, particularly preferably 0.0001 to 0.001. This may simultaneously provide for a high reaction rate and a particularly low byproduct formation.

The method according to the invention may optionally be conducted batchwise, semicontinuously, or continuously, the continuous embodiment being particularly economical to operate on an industrial scale of greater than 10 000 tons/a.

The MMP-cyanohydrin produced according to the invention may have the following composition:
MMP-CN: 86-97% by weight,
MMP: 0-1% by weight,
HCN: 0.05-0.5% by weight,
$H_2O$: 2-14% by weight,
Oligomers: 0.01-0.1% by weight.

The molar yields based on MMP are typically 99.50 to 99.99%.

The reaction product containing methylthiopropionaldehyde cyanohydrin (MMP-cyanohydrin) obtained in accordance with the method according to the invention may, particularly advantageously, be used directly for producing methionine and 2-hydroxy-4-methylthiobutyric acid. For this purpose, it may be either aminated (aminonitrile pathway) or reacted with a mixture of ammonia and carbon dioxide (hydantoin pathway), in order to form methionine or hydrolyzed directly to form 2-hydroxy-4-methylthiobutyric acid (methioninehydroxy analogs, MHA). It has, furthermore, surprisingly been found that high-boiling MMP oligomers already present in MMP may for the most part, be reacted in the method according to the invention to form the desired MMP-cyanohydrin. This may be shown in that, e.g., the residue formed in the distillation of the products is markedly less after the reaction than before the reaction to form the MMP-cyanohydrin.

Having generally described this invention, a further understanding may be obtained by reference to certain specific examples which are provided hereinafter, for purposes of illustration only, and are not intended to be limiting unless otherwise specificed.

Analytical methods used:

The $H_2O$ content in MMP-CN was determined by the method of titration with biamperometric indication of the end point (Karl-Fischer titration).

For this purpose, 20-30 ml of titration medium (e.g. Hydranal Solvent 5, Fluka) were charged into the titration vessel and titrated to dryness using titration agent (e.g. Hydranal Titrant 5, Fluka). A sample quantity of approximately 500 mg was added to the initial charge that had been titrated to exhaustion (plastic disposable syringe) and titrated to the end point with titration agent. The exact sample weight was determined by differential weighing.

The procedure of this standard method is known to those skilled in the art (see, e.g., P. A. Bruttel, R. Schlink: Wasserbestimmung durch Karl-Fischer-Titration [Water determination by Karl-Fischer titration] Metrohm AG).

The free prussic acid content of the product was determined by the principle of ion chromatography (IC) using amperometric cyanide detection at an Ag working electrode, the sample preparation having proceeded by separating off the free prussic acid from the sample matrix by means of preparative column chromatography.

The preparative cyanide removal was performed, e.g., at room temperature, on a PRP-X 300 separation column, 250 mm length×4.1 mm internal diameter from Hamilton. The mobile phase consisted of a 5 mmolar sulfuric acid. At a flow rate of 1.0 ml/min, 100 µl of the sample solution (0.1 g of sample in 10 ml of mobile phase) were injected. The column eluate from 4 min to 8 min was collected in a 100 ml measuring flask, made up to the mark with ultrapure water and 100 µl were injected into the IC for cyanide determination.

Similarly to the sample solution, an NaCN calibration solution of known content was subjected to the preparative separation by means of column chromatography and 100 µl were injected into the IC for cyanide determination.

The ion-chromatographic cyanide determination was carried out at room temperature, e.g. on a Carbo Pac PA1 separation column, 250 mm in length×4.0 mm internal diameter from Dionex. The mobile phase consisted of a solution of 1.5 g of sodium chloride and 1 ml of ethylenediamine in 1 l of a 50 mmolar sodium hydroxide solution. At a flow rate of 1.0 ml/min, 100 µl of sample solution or calibration solution were injected. The evaluation was performed by peak area comparison using the external standard method.

The procedure of this standard method is known to those skilled in the art.

The MMP-CN and MMP contents of the product were determined by means of isocratic ion exclusion chromatography on a cation exchanger with subsequent UV detection at 205 nm. The determination was carried out, e.g., on a PRP-X 300 separation column, 250 mm in length×4.1 mm internal diameter from Hamilton at a temperature of 25° C. The mobile phase consisted of a 5 mmolar sulfuric acid. At a flow rate of 1.0 ml/min, 1000 of the respective sample solution (0.5 g of sample for MMP determination or 0.06 g of sample for MMP-CN determination in 50 ml of solvent) were injected. The calibration proceeded by injecting suitable calibration solutions (0.5 mg of MMP in 50 ml of solvent, or 50 mg of MMP-CN in 50 ml of solvent).

The solvent consisted of a mixture of 500 µl of 0.5 molar $H_2SO_4$ and 5 ml of acetonitrile which was diluted to 50 ml with ultrapure water.

The evaluation proceeded by peak area comparison by means of the external standard method.

The procedure of this standard method is known to those skilled in the art.

The components in the HCN-containing starting material gas nitrogen ($N_2$), carbon monoxide (CO), carbon dioxide ($CO_2$), methane ($CH_4$), ammonia ($NH_3$), prussic acid (HCN), water ($H_2O$), argon (Ar)/oxygen ($O_2$) (either/or), hydrogen ($H_2$) (only conditionally) and benzene as internal standard were determined by gas chromatography. The gas chromatograph 6890 (Agilent, based on the HP 6890) was used here. The gas chromatograph for this analysis was equipped with three separation columns: 1. HP-CPWAX 52CB 25 m*0.32 mm*0.2 µm (here NH3, HCN, water and benzene were separated), 2. molecular sieve 30 m*0.32 mm*12 m (here $H_2$, $N_2$, $O_2$, CO and methane were separated) and 3. PlotQ 30 m*0.32 mm*20 µm (here $CO_2$ and benzene were separated), two thermal conductivity detectors (TCD), a pressure measuring unit and a mass flow meter (MFM) for helium. Column 1 was connected via a back injector to the back detector. Columns 2 and 3 were connected by a front injector to the front detector.

The procedure of this standard method is known to those skilled in the art.

The components methylmercaptan (MC) and methylmercaptopropionaldehyde (MMP) and acrolein (AC) of the residual gas exiting from the column top were determined by means of gas chromatography. In this case the gas chromatograph 7890A (Agilent) was used. The gas chromatograph was equipped for this analysis with a separation column (HP-INNOWAX 60 m*0.32 mm*0.25 µm) and a back detector (FID). The procedure of this standard method is known to those skilled in the art.

Example 1

A setup as shown in FIG. 1 was used, having a column of 70 mm in diameter, which was equipped with 2 ordered packings (C) and (E) and which had heights in each case of 2500 and 1700 mm. Between the ordered packings were situated an intermediate bottom phase (D), from which a stream (6) can be taken off for operating a top circuit. Beneath the column was situated the column bottom phase having a volume of 4 liters. The diagram of this device is attached (see FIG. 1).

With the stream (1), 8.98 kg/h of crude product gas from the production of hydrogen cyanide by the Andrussow method were fed via the gas blower (B) into the column bottom phase A which contained, based on weight: HCN: 8.87%, $H_2O$: 3.88%, $H_2$: 1.33%, $N_2$: 76.01%, $O_2$: 1.48%, CO: 5.67%, $CO_2$: 1.13%, $CH_4$: 0.39%. The incoming gas was mixed at the jet pump (B) with a circulating stream (8) of 300 kg/h. The temperature of the circulation stream was controlled here in such a manner that in the column bottom phase (A), at a filling state of 50%, a temperature of 50° C. prevailed. The feed stream (7) onto the ordered packing (C), at 40 kg/h, had a temperature of 35° C.

The methylthiopropionaldehyde was introduced into the reactor (G) via the feed (2) at a throughput of 2.966 kg/h. The reactor contained, based on weight:

MMP: 96.46%, $H_2O$: 2.77%, MC: 0.2%. Via the feed line (3), at the same time 0.211 kg/h of a mixture of 99% by weight of MMP in the composition described above and 1% by weight of triethanolamine as catalyst were introduced into the reactor (G). The whole stream (5) consisting of the starting materials and the circulation stream (6) was 40 kg/h in the feed to the upper ordered packing (E) at a temperature of 6° C.

The molar starting material ratio HCN/MMP was 1. The product left the column bottom phase at 4.20 kg/h and had the following composition, based on weight: MMP-CN: 90.43%, $H_2O$: 7.82%, MMP: 0.14%, HCN: 0.16%, MC: 0.01%. The exhaust gas left the column top at 8.07 kg/h and had the following composition based on weight: HCN: 0.00%, MMP: 0.07%, MC: 0.05%, $H_2O$: 1.34%, $H_2$: 1.48%, $N_2$: 86.02%, $O_2$: 1.64%, CO: 6.31%, $CO_2$: 1.26%, $CH_4$: 0.44%. The gases were fed to a combustion plant.

Example 2

The setup of Example 1 was used.

With the stream (1), 8.94 kg/h of crude product gas of the production of hydrogen cyanide by the Andrussow method were fed via the gas blower (B) into the column bottom phase A which contained, based on weight: HCN: 8.9%, $H_2O$: 3.7%, $H_2$: 1.3%, $N_2$: 76.3%, $O_2$: 1.5%, CO: 5.6%, $CO_2$: 1.1%, $CH_4$: 0.4%. The incoming gas was mixed at the jet pump (B) with a circulating stream (8) of 280 kg/h. The temperature of the circulation stream was controlled in this case in such a manner that, in the column bottom phase (A), at a filling state of 50%, a temperature of 49.8° C. prevailed. The feed stream (7) onto the ordered packing (C) had a temperature of 35° C. at 40 kg/h.

The methylthiopropionaldehyde was introduced into the reactor (G) via the feed (2) at a throughput of 2.976 kg/h. It contained, based on weight:

MMP: 96.9%, $H_2O$: 2.8%, MC: 0.2%. Via the feed line (3), at the same time, 0.2 kg/h of a mixture of 99% by weight of MMP in the above described composition and 1% by weight of triethanolamine as catalyst was introduced into the reactor (G). In addition, 2 kg/h of the bottom phase product were introduced via the pathway (13) into the reactor (G). The whole stream (5) consisted of the starting materials and the circulation stream (6) and the product stream (13) was 42 kg/h in the feed to the upper ordered packing (E) at a temperature of 5.5° C.

The molar starting material ratio HCN/MMP corresponded to 1. The product left the column bottom phase at 4.25 kg/h and had the following composition, based on weight:

MMP-CN: 90.06%, $H_2O$: 8.81%, MMP: 0.75%, HCN: 0.21%, MC: 0.01%. The exhaust gas left the column top at 7.88 kg/h and had the following composition based on weight:

HCN: 0.00%, MMP: 0.09%, MC: 0.10%, $H_2O$: 0.6%, $H_2$: 1.50%, $N_2$: 86.60%, $O_2$: 1.70%, CO: 6.40%, $CO_2$: 1.20%, $CH_4$: 0.50%. The gases were fed to a combustion plant.

The invention claimed is:

1. A process for producing D,L-methionine, the process comprising:
    conversion of 2-hydroxy-4-(methylthio)butyronitrile to the D,L-methionine by reaction with ammonia, optionally in the presence of carbon dioxide;
    wherein
    the 2-hydroxy-4-(methylthio)butyronitrile is obtained by a process comprising:
    reacting 3-methylmercaptopropionaldehyde with hydrogen cyanide in the presence of a base as catalyst in a main reaction zone of a multizone reactor to form a reaction mixture comprising the 2-hydroxy-4-(methylthio)butyronitrile, unreacted 3-methylmercaptopropionaldehyde, the catalyst and residual amounts of gaseous hydrogen cyanide;
    removing the residual gaseous hydrogen cyanide from the main reaction zone to an absorption and post-reaction zone of the reactor which comprises a mixture of 3-methylmercaptopropionaldehyde and the catalyst;
    further reacting the gaseous hydrogen cyanide with the 3-methylmercaptopropionaldehyde in the absorption and post reaction zone; and
    removing the 2-hydroxy-4-(methylthio)butyronitrile from the multizone reactor.

2. The process according to claim 1, wherein a pH of the reaction mixture in the main reaction zone of the 3-methylmercaptopropionaldehyde hydrogen cyanide reaction and the absorption and post-reaction zone is 4.5 to 6.0, as measured with a pH electrode at 23° C. and a water content of 2 to 14% by weight.

3. The process according to claim 1, wherein the main reaction zone comprises a jet pump and the jet pump mixes a hydrogen cyanide feed gas with the reaction mixture.

4. The process according to claim 1, wherein the absorption and post-reaction zone comprises a device for contacting a gas with a liquid, the device being at least one selected from the group consisting of a column, a tray column, a packed-bed column, a bubble-column reactor, a droplet column, a reactor having a mechanically agitated container, a submerged jet reactor and a jet pump.

5. The process according to claim 1, wherein the catalyst is selected from the group consisting of a low-molecular-weight amine, a heterogeneous amine, a solution of an inorganic base, and a mixture of an acid and a low-molecular-weight amine.

6. The process according to claim 5, wherein the catalyst is a low-molecular-weight amine, which is selected from the group consisting of a tri-($C_1$-$C_{12}$-alkyl)amine, a dialkylaralkylamine, a dialkylarylamine and a heterocyclic amine.

7. The process according to claim 6, wherein the catalyst is a polyvinylpyridine or a heterogeneous amine which is of formula (I)

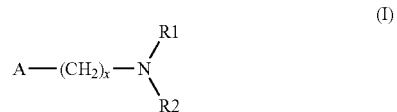

wherein
$R_1$ and $R_2$ are each independently hydrogen, $C_1$ to $C_{12}$alkyl, aryl or heteroaryl;
X is a number between 0 and 6, and
A is a natural or synthetic resin.

8. The process according to claim 7, wherein the catalyst is a heterogeneous amine of formula I and is a polymer-bound base selected from the group consisting of homologous dialkylaminoalkylpolystyrenes and dialkylaminomacroreticular resins.

9. The process according to claim 8, wherein the catalyst of formula I is at least one selected from the group consisting of diethylaminoethylpolystyrene, diethylaminomethylpolystyrene, dimethylaminomethylpolystyrene, diethylaminomethylmacroreticular resin and dimethylaminoethylpolystyrene.

10. The process according to claim 5, wherein the catalyst is an inorganic base which is at least one selected from the group consisting of an alkali metal hydroxide, an alkali metal cyanide, an alkali metal carbonate, and an alkali metal hydrogencarbonate.

11. The process according to claim 5, wherein the catalyst is a mixture of an acid and a low-molecular-weight amine and the acid is at least one selected from the group consisting of organic carboxylic acids, organic sulfonic acids and mineral acids.

* * * * *